United States Patent [19]
Horn

[11] Patent Number: 4,719,441
[45] Date of Patent: Jan. 12, 1988

[54] SENSOR FOR MEASURING ELECTRICAL CONDUCTIVITY

[75] Inventor: Petr Horn, Oberhasli, Switzerland

[73] Assignee: Navasina AG, Zurich, Switzerland

[21] Appl. No.: 830,516

[22] Filed: Feb. 14, 1986

[30] Foreign Application Priority Data

Feb. 26, 1985 [CH] Switzerland .................... 872/85

[51] Int. Cl.⁴ .............................. H01C 7/10
[52] U.S. Cl. ................... 338/20; 338/306; 338/307; 338/308; 29/611
[58] Field of Search .......... 338/22 R, 22 SD, 25, 338/20, 306–308; 29/611, 612; 73/362 AR; 427/127, 125, 96

[56] References Cited

U.S. PATENT DOCUMENTS

| | | | |
|---|---|---|---|
| 4,073,970 | 2/1978 | Allen | 338/308 X |
| 4,139,833 | 2/1979 | Kirsch | 338/308 |
| 4,463,337 | 7/1984 | Håkanson | 338/25 X |
| 4,464,646 | 8/1984 | Burger et al. | 338/25 |

Primary Examiner—Clifford C. Shaw
Assistant Examiner—M. M. Lateef
Attorney, Agent, or Firm—Ladas & Parry

[57] ABSTRACT

At least two electrodes (1, 2) each provided with at least one lead (5) are applied in the form of conductor tracks to a substrate. The leads (5) can be made of a material having a lower standard potential than that of the electrodes (1, 2). A dielectric (6) covers the electrode ends and, up to the contact points (4), the leads (5). As required, the electrodes (1, 2) can be designed and used as a heating electrode and/or as a temperature sensor. Moreover, the electrodes can be arranged on one side or on both sides of the substrate board (7).

11 Claims, 3 Drawing Figures

SENSOR FOR MEASURING ELECTRICAL CONDUCTIVITY

The present invention relates to a sensor for measuring electrical conductivity, the sensor having at least two heat-resistant and/or corrosion-resistant spaced electrodes provided with leads.

In various cases, sensors for measuring electrical conductivity can be exposed to high temperatures and/or corrosive environments. Both these points apply, for example, to devices for monitoring combustion processes. In addition to high exit gas temperatures, they must also be able to withstand hot sulfuric acid vapors, nitrogen oxides and the like.

German Patent Specification No. 2,631,027 C3 discloses a device for the detection of solid or liquid substances in the event of incomplete combustion of fuel, wherein the quantity of the precipitated substances is measured by means of a sensor. The sensor additionally contains a heating element for pyrolytic self-cleaning after a measuring operation. This sensor has the disadvantage that it is expensive to manufacture and that it requires a relatively large amount of space. Moreover, a large amount of energy is required for heating such a sensor, because of its large mass.

The invention as defined in the claims achieves the object of providing a sensor for measuring electrical conductivity which requires little space, can be heated with relatively modest energy consumption when required and can be manufactured inexpensively.

The invention is explained below in more detail by way of example with reference to a drawing in which.

Figure 1:
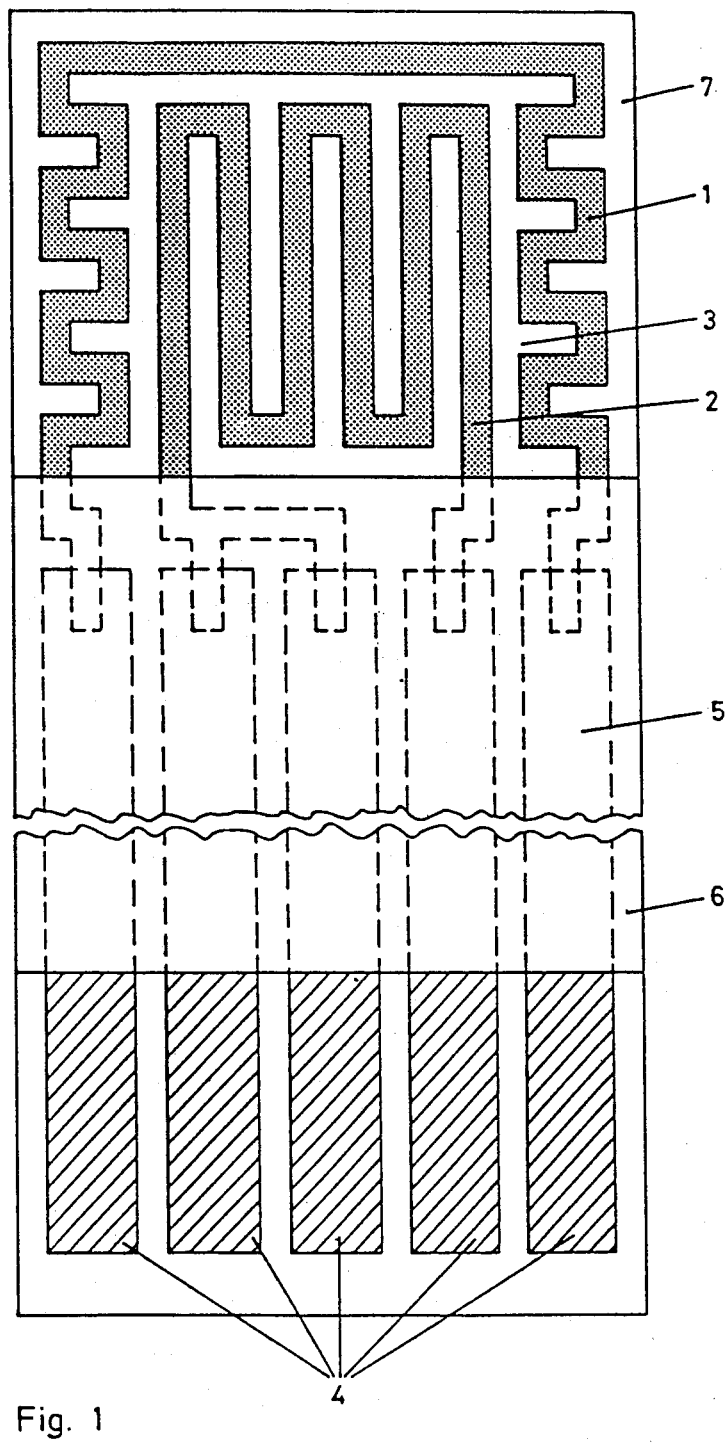
FIG. 1 is a plane view of a sensor with electrodes on one side of a substrate board.

The sensor according to FIG. 1 has two electrodes 1 and 2 in the form of conductor tracks exposed on a ceramic substrate board 7. The measuring area 3 is located between the electrodes 1 and 2. Electrically conductive leads 5 are applied above the electrode ends and overlapping the latter. Except for the ends serving as contact points 4, the leads 5 are covered by a dielectric 6. The dielectric 6 thus determines the measuring area 3 used for the conductivity measurement. In this way it is possible to provide a precisely reproducible measuring area 3 for all sensors.

The electrical conductivity of the substance present on the measuring area 3 is measured between the electrodes 1 and 2. The electrical conductivity of a material is dependent on its temperature. This can be measured continuously by means of the inner electrode 2 which is designed as a temperature sensor. An electrode envisaged for temperature measurement can be provided with a 2-wire, 3-wire or 4-wire lead. The embodiment shown in FIG. 1 allows a temperature measurement in accordance with the principle of a 3-wire lead. The outer electrode 1 is provided with two leads 5 and can be used as a heating electrode. Using the electrode 1, the temperature of the sensor can be varied and hence a thermal analysis of the substance being measured can be carried out. In this case, the temperature is slowly raised and the electrical conductance of the substance is measured as a function of the temperature. By means of a thermal analysis, the following operating states can be detected, for example in an oil-fired furnace:

temperature below the water dew point
temperature below the acid dew point
soot
oil residues in the exit gas.

By means of the heating electrode 1, the sensor can also be heated up to such an extent that the substances present on it are completely burned. This process is called self-cleaning. Both during the thermal analysis and during self-cleaning, the temperature can be monitored continuously by means of the inner electrodes 2 having three leads 5.

A measurement of combustion processes can be carried out as follows:

The sensor is continuously exposed to the combustion exit gases. For this purpose, it is fitted, for example, in a stack or in an exhaust pipe. When the equipment to be monitored is in operation, the electrical conductivity is in each case continuously monitored for a certain period which is called the reference time. After a given period has expired, self-cleaning is initiated. However, self-cleaning takes place already at an earlier stage if the conductivity falls below a given minimum. In this case, an alarm signal is triggered additionally.

The electrodes 1, 2 are applied in the form of conductor tracks to a ceramic (i.e., electrically-insulating and heat-resistant and/or corrosion-resistant) substrate board 7 by the thin-film technology and/or the thick-film technology. The substrate board 7 preferably consists of alumina to the extent of more than 95%. However, examples of other substrate materials are beryllium oxide, porcelain or enameled steel substrates. In order to be able to withstand the high temperatures and the corrosive environment, the electrode material consists of a noble metal or a high-grade alloy. The nobler a metal or the higher the grade of an alloy, the higher is the corresponding standard potential. Platinum has proved to be an outstandingly suitable electrode material. Platinum/gold alloys, titanium, tungsten, vanadium and many others are also suitable. High temperatures are generated in particular during self-cleaning. It is therefore not possible to employ the materials normally used for conventional circuit technology. The temperature decay is obtained by means of leads 5 of appropriate length, which are likewise applied to the substrate board 7. In the region of the heating electrode 1, the electrodes 1, 2 are regularly cleaned by the self-cleaning method. However, this is not possible for the leads 5. On these, impurities can accumulate in the course of time. Such impurities generate tracking currents which can falsify the measurements. For this reason, the leads are covered by a heat-resistant and corrosion-resistant dielectric 6, such as is used, for example, in thick-film technology. Every manufacturer uses a somewhat different dielectric 6, and this is part of his know-how. Any dielectric materials can be used which are compatible with the material of the leads and remain adhering to the latter and which can be fired at a temperature lower than the firing temperature of the conductor material.

Like the electrodes 1, 2, the leads 5 can also consist of platinum. Platinum has, however, the disadvantage that, on the one hand, it is very expensive and, on the other hand, it is difficult to contact, i.e., bond to. Microwelding requires a substantially thicker platinum layer than would be necessary for measurement purposes. As a result, the manufacturer of the sensor would become much more expensive. The contacting of platinum is particularly critical, when the contact points are exposed to vibrations such as occur, for example, in oil burners and internal combustion engines. It has proved to be an advantageous solution to make the leads 5 of silver/palladium. Silver/palladium is substantially cheaper than platinum. It can likewise be exposed to high temperatures. However, it is not corrosion-resistant. Nevertheless the leads 5 are protected from corrosion by the dielectric 6. Further possible materials for the leads are platinum/silver alloys, platinum/palladium/silver alloys, platinum/gold/silver alloys and palladium/gold alloys.

The sensor can be produced by the following operations:

In a first operation, the electrodes 1, 2 are applied to the substrate board 7 by a thin-film and/or thick-film process.

In a second operation, the leads 5 are applied by the thick-film process. The leads 5 overlap the electrodes in order to ensure good contacting. The temperature at which the leads 5 are fired is below the melting point of the electrode material.

In a third operation, the dielectric 6 is applied. It is fired at a temperature which is below the melting point of silver/palladium. The dielectric 6 covers the areas where the leads 5 overlap the electrode connections. The ends of the leads 5, located on the side remote from the electrodes 1 and 2, are left free as contact points 4.

In a fourth operation, the contact points 4 can be tin-plated in order to improve the solderability. The tin-plating additionally protects them also from oxidation.

Figures 2, 3:
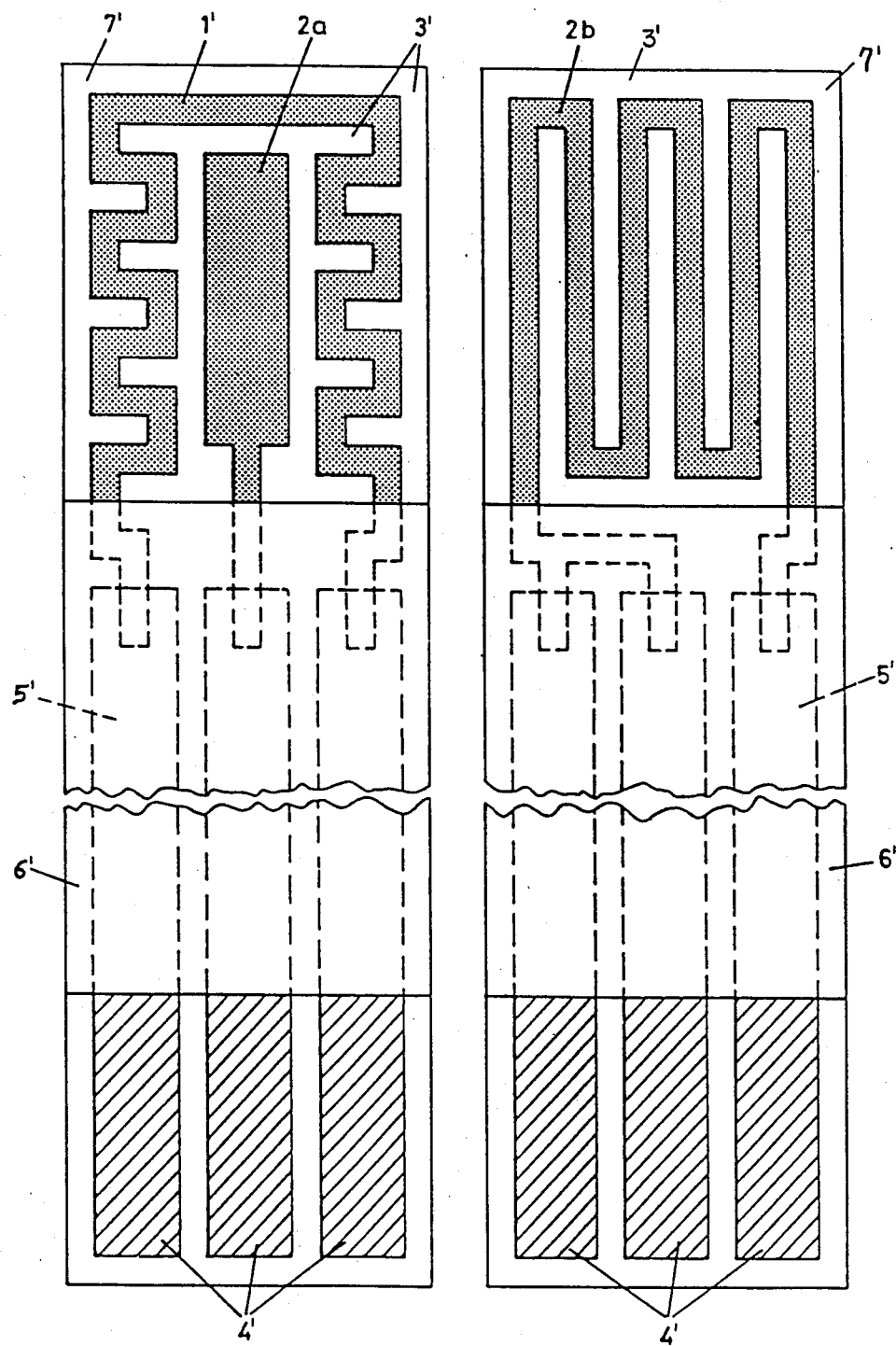
FIG. 2 is a plane view of another sensor with electrodes on both sides of a substrate board.
FIG. 3 is a bottom view of the sensor of FIG. 2.

FIGS. 2 and 3 show, respectively, the front and rear of a further embodiment of a sensor according to the invention. The sensor shown here differs from that according to FIG. 1' in that electrodes, 1, 2a, 2b provided with leads 5', as well as a dielectric 6' and contact points 4' are provided on both sides of the substrate board 7' spaced portions of the electrode 1' are, respectively, overlapped two leads 5: The electrode, which is for heating and, at the same time, for measuring electrical conductivity, surrounds a counter-electrode 2a. The temperature sensor 2b provided with three leads 5' and, fitted to the rear, serves as a further counter-electrode. The measuring area 3' consequently also extends around the edges, surrounding the electrodes 1', 2b, of the substrate board 7'. This has the advantage that a lateral edge of a sensor to be exposed to the exit gases can be directed against the exit gas stream. By this means, the abrasive effect exerted by solid particles, (for example iron oxide) flying against on the conductor tracks, can be greatly reduced. The electrical conductivity of the impurities depositing in the edge zones and on the edge can be measured between the electrodes 1' and 2b. However, it is also possible, as in the embodiment shown in FIG. 1, to direct the front face against the exit gas stream and to measure the electrical conductivity between the electrodes 1' and 2a.

A further advantage of the embodiment of FIGS. 2 and 3 is that the leads 5 are distributed over two sides. This allows a considerable reduction in the width of a sensor.

In a greatly simplified embodiment, it would be possible to build a sensor which has electrodes on only one side according to FIG. 2. The heating electrode 1 could also be used alternately for measuring the temperature. Although this would not allow a temperature measurement as precise as with a 3-wire temperature sensor, this might be sufficient in many cases. However, even here a 3-wire connection or 4-wire connection could be provided.

In the simplest embodiment, in which neither heating nor temperature measurement is required, it would also be possible to provide only two electrodes, each with one lead and one contact, either together on one substrate side or opposite one another on either substrate side.

I claim:

1. A sensor for measuring electrical conductivity, comprising:
   an electrically-insulating substrate, the substrate being one of heat and corrosion resistant
   at least two, spaced electrodes exposed on the substrate, the electrodes being one of heat and corrosion resistant;
   at least two electrically-conductive leads on the substrate, one end of each lead overlapping a portion of a respective one of the electrode; and
   a dielectric covering the leads, the dielectric being one of heat and corrosion resistant whereby to define a measuring area of the exposed electrodes on one side of the one, dielectric-covered, lead-overlapped ends of the electrodes, except for a contact-point portion of each lead at the other end thereof, remote from the one end overlapping the electrode, whereby to define a contact point thereat.

2. A sensor as claimed in claim 1, wherein the electrodes and the leads are made of different materials, the electrode material having a higher standard potential than the material of the leads.

3. A sensor as claimed in claim 1, wherein the electrodes consist of platinum.

4. A sensor as claimed in claim 1, wherein the substrate is made of alumina to the extent of more than 95%.

5. A sensor as claimed in claim 3, wherein the leads consist of silver/palladium.

6. A sensor as claimed in claim 5, wherein the leads have tin-plated contact points.

7. A sensor as claimed in claim 1, wherein one electrode is arranged on the other side of the substrate relative to the remaining electrodes.

8. A sensor as claimed in claim 1, wherein one of the two electrodes has at least two leads for use as one of a heating electrode and a temperature sensor.

9. A sensor as claimed in claim 1, wherein one electrode has two leads for use as a heating element, and another electrode has at least two leads for use as a temperature sensor.

10. A process for the production of the sensor as claimed in claim 2, which comprises, a first operation of applying electrodes to a substrate, a second operation of applying leads to the substrate and firing them at a temperature below the melting point of the electrodes, and finally, a third operation of applying a dielectric to the substrate and firing it at a temperature below the melting point of the leads.

11. A method of measuring electrical conductivity, comprising:
   providing an electrically-insulating substrate, the substrate being one of heat and corrosion resistant;
   providing at least two, spaced electrodes exposed on the substrate, the electrodes being one of heat and corrosion resistant;
   providing at least three electrically-conductive leads on the substrate, one end of one lead overlapping a portion of one of the electrodes and one end of the other two leads overlapping spaced portions of the other electrode;

providing a dielectric covering the leads, the dielectric being one of heat and corrosion resistant, whereby to define a measuring area of the exposed electrodes on one side of the one, dielectri-covered, lead-overlapped ends of the electrodes, except for a contact-point portion of each lead at the other end thereof, remote from the one end overlapping the electrode, whereby to define a contact point thereat;

applying an electric potential across the contact point portions of the other two leads to heat the electrode overlapped thereby conductively sufficiently to clean off a deposit on the substrate between the electrodes; and sensing the electrical conductivity of the deposit at the contact point portion of the one electrode while so applying the electric potential.

* * * * *